United States Patent [19]
Leeb et al.

[11] 4,301,160
[45] Nov. 17, 1981

[54] READY FOR USE, INJECTABLE, AQUEOUS SOLUTIONS OF ALKALI METAL SALTS OF CANRENOIC ACID AND FUROSEMIDE AND PROCESS FOR THEIR PREPARATION

[75] Inventors: Richard Leeb, Kelkheim; Rainer J. Helbig, Frankfurt am Main, both of Fed. Rep. of Germany

[73] Assignee: Hoechst Aktiengesellschaft, Frankfurt am Main, Fed. Rep. of Germany

[21] Appl. No.: 216,957

[22] Filed: Dec. 16, 1980

[30] Foreign Application Priority Data

Dec. 18, 1979 [DE] Fed. Rep. of Germany ....... 2950832

[51] Int. Cl.$^3$ ............................................. A61K 31/58
[52] U.S. Cl. .................................................... 424/241
[58] Field of Search ....................... 424/241; 260/397.1

[56] References Cited

U.S. PATENT DOCUMENTS 3,919,198 11/1975 Warnant et al. ................. 260/397.1

OTHER PUBLICATIONS

Chinn et al., "J. Org. Chem.," vol. 40, No. 9, (1975), pp. 1328–1331.

Primary Examiner—Elbert L. Roberts
Attorney, Agent, or Firm—Curtis, Morris & Safford

[57] ABSTRACT

Ready for use, injectable, aqueous solution of a pH of from 10.2 to 11.2 containing a mixture of an alkali metal salt of canrenoic acid and furosemide without addition of a buffer and process for their preparation.

5 Claims, No Drawings

READY FOR USE, INJECTABLE, AQUEOUS SOLUTIONS OF ALKALI METAL SALTS OF CANRENOIC ACID AND FUROSEMIDE AND PROCESS FOR THEIR PREPARATION

The invention relates to ready for use, injectable, aqueous solutions of a mixture of the alkali metal salts of canrenoic acid and furosemide. The solutions do not contain a buffer, they can be sterilized and are stable and locally tolerable.

Canrenoic acid (3-(3-oxo-17$\beta$-hydroxy-4,6-androstadien-17$\alpha$-yl)-propionic acid) and its potassium salt (K-canrenoate) as well as furosemide (4-chloro-N-(2-furylmethyl)-5-sulfamoyl-anthranilic acid) are being used in medicine as diuretics. A combination preparation for injection containing an alkali metal canrenoate/diuretic mixture has also been described. DE-PS 2,556,001 claims, inter alia, an alkaline solution ready for injection consisting of an alkali metal canrenoate/diuretic mixture, water and a physiologically acceptable alkaline buffer, characterized in that the solution has a pH of 10.2 to 11.2 and that the capacity of the buffer does not exceed 0.1 gram-equivalent per liter of injection solution in the indicated pH range. In the specification it is indicated that a stable solution, which is physiologically acceptable when injected and capable of being sterilized at 120° C. must have the aforesaid properties. It is essential that the solution has the specified pH and contains a buffer of minor capacity besides the active substances.

Contrary to the statements in the aforesaid specification, it has now been found, surprisingly, that solutions having the aforesaid properties, containing a mixture of alkali metal salts of canrenoic acid and furosemide of a pH above 10 need not contain a buffer. Aqueous solutions of this type exclusively containing the active substances in the form of their alkali metal salts and optionally suitable additives to render them isotonic, such as, for example, sodium chloride, but not additional buffer, ensure an optimum physiological tolerance without having any disadvantages, as regards stability and sterilizability, over the solutions of the above patent specification. The solutions according to the invention are used as medicaments.

The present invention provides ready for use, injectable, aqueous solutions of a pH of from 10.2 to 11.2, characterized in that they contain a mixture of alkali metal salts of canrenoic acid and furosemide without addition of a buffer.

The solutions of the invention, which are free from buffer, preferably have a pH of from 10.6 to 11.0, more preferably of 10.8.

Potassium canrenoate is the preferred alkali metal canrenoate and furosemide is preferably used in the form of its sodium salt. The proportion of alkali metal canrenoate to furosemide is preferably in the range of from 30:1 to 5:1, more preferably 10:1. A dosage unit (1 ampoule) preferably contains 100 to 400 mg, more preferably 200 mg, of alkali metal canrenoate. The alkali metal canrenoate concentration in the aqueous solution is preferably in the range of from 4% to 0.5%, more preferably 1% to 2%.

It is another object of the invention to provide a process for the manufacture of ready for use, injectable, aqueous solutions of a pH of from 10.2 to 11.2, which comprises suspending canrenoic acid or an alkali metal canrenoate and furosemide in water and adjusting the pH of the suspension to 10.2-11.2 by adding aqueous alkali solution, thereby transforming the suspension into a clear solution. Suitable alkali solutions are, in the first place, alkali metal hydroxide solutions, preferably sodium hydroxide solution.

In the case of free canrenoic acid being used and adjusting the desired pH by means of alkali solution, the two active substances are contained in the solution as salts with the same cation.

It is recommended to produce the solution under an inert gas, for example nitrogen.

The solutions of the invention are stable, they can be sterilized at 120° C., they are well tolerated physiologically and they can be injected intravenously without previous dilution. An administration as short time infusion, optionally with addition of glucose infusion solution or agents for tendering the solution isotonic, such as, for example, sodium chloride, is likewise possible.

The following examples illustrate the invention.

EXAMPLE 1

All process steps are carried out under inert gas, for example nitrogen. 10 g of potassium canrenoate are dissolved and 1 g of furosemide is suspended in 800 ml of water for injection purposes. The furosemide is dissolved by adding sodium hydroxide solution while stirring and the pH of the solution is adjusted at 10.8. The solution is made up to 1 liter with water for injection purposes. The solution is sterile-filtered, filled into ampoules of 20 ml and the ampoules are sterilized for 20 minutes at 120° C.

EXAMPLE 2

All process steps are carried out under inert gas, for example nitrogen. 20 g of potassium canrenoate are dissolved and 2 g of furosemide suspended in 800 ml of water for injection purposes. The furosemide is dissolved by adding sodium hydroxide solution while stirring and the pH of the solution is adjusted to 10.8. The solution is made up to 1 liter with water for injection purposes. The solution is sterile-filtered, filled into ampoules of 10 ml and the ampoules are sterilized for 20 minutes at 120° C.

What is claimed is:

1. Ready for use, injectable, aqueous solution of a pH of from 10.2 to 11.2, characterized in that it contains a mixture of an alkali metal salt of canrenoic acid and furosemide without addition of a buffer.

2. Solution as claimed in claim 1, containing potassium canrenoate and the sodium salt of furosemide.

3. Process for the manufacture of a ready for use, injectable, aqueous solution of a pH of from 10.2 to 11.2, which comprises suspending canrenoic acid or an alkali metal canrenoate and furosemide in water and adjusting the pH of the suspension to 10.2-11.2 by adding aqueous alkali solution, thereby transforming the suspension into a clear solution.

4. Process as claimed in claim 3, wherein potassium canrenoate and furosemide are suspended in water and the suspension is adjusted to pH 10.2 to 11.2, preferably 10.6 to 11.0, with sodium hydroxide solution.

5. Process as claimed in claims 3 or 4, wherein the pH is adjusted to 10.8.

* * * * *